US006087558A

United States Patent [19]
Howard et al.

[11] Patent Number: 6,087,558
[45] Date of Patent: Jul. 11, 2000

[54] COMMERCIAL PRODUCTION OF PROTEASES IN PLANTS

[75] Inventors: John A. Howard; Elizabeth Hood, both of College Station, Tex.

[73] Assignee: ProdiGene, Inc., College Station, Tex.

[21] Appl. No.: 09/120,582

[22] Filed: Jul. 22, 1998

[51] Int. Cl.$^7$ .............................. A01H 5/10; A01H 5/00; C12N 5/04; C12N 15/57; C12N 15/12; C12N 15/82

[52] U.S. Cl. ...................... 800/278; 435/69.1; 435/69.8; 435/412; 435/419; 435/468; 800/287; 800/288; 800/295; 800/298; 800/306; 800/320.1

[58] Field of Search ............................. 435/69.1, 320.1, 435/410, 412, 419, 468, 69.8; 536/24.1; 800/278, 287, 288, 295, 298, 306, 320.1

[56] References Cited

U.S. PATENT DOCUMENTS

| | | | |
|---|---|---|---|
| 5,097,025 | 3/1992 | Benfey et al. | 536/27 |
| 5,122,594 | 6/1992 | Yoshida et al. | 530/324 |
| 5,215,912 | 6/1993 | Hoffman | 435/240.4 |
| 5,270,200 | 12/1993 | Sun et al. | 435/240.2 |
| 5,290,924 | 3/1994 | Last et al. | 536/24.1 |
| 5,358,934 | 10/1994 | Borovsky et al. | 514/17 |
| 5,424,200 | 6/1995 | McPherson et al. | 435/70.1 |
| 5,457,066 | 10/1995 | Frank et al. | 435/68.1 |
| 5,504,200 | 4/1996 | Hall et al. | 536/24.1 |
| 5,543,501 | 8/1996 | Slingtom et al. | 530/350 |
| 5,552,527 | 9/1996 | Godlard et al. | 530/329 |
| 5,629,196 | 5/1997 | Borovsky et al. | 435/418 |
| 5,693,520 | 12/1997 | Branner | 435/213 |
| 5,714,580 | 2/1998 | Brunck et al. | 530/331 |
| 5,741,664 | 4/1998 | Ballinger et al. | 435/68.1 |

FOREIGN PATENT DOCUMENTS

| | | | |
|---|---|---|---|
| 0597681 | of 1993 | European Pat. Off. | C12N 9/76 |
| 265 164 | 2/1989 | Germany | C12N 15/00 |
| WO 92/01042 | 1/1992 | WIPO | C12N 5/14 |
| WO 95/14099 | 5/1995 | WIPO | C12N 15/82 |
| WO 96 21033 | 7/1996 | WIPO | C12N 15/82 |
| WO 98/36085 | 8/1998 | WIPO | C12N 15/82 |

OTHER PUBLICATIONS

Wyatt, Paul et al. "Correct processing of the kiwifruit protease actinidin in transgenic tobacco requires the presence of the C-terminal propeptide" *Plant Physiol.* 108(1), 261–8 (1995).

van der Geest, A. and Hall, T. "A 68 bp element of the beta–phaseolin promoter functions as a seed–specific enhancer" *Plant Molecular Biology* 32:579–588 (1996).

Christensen et al, Plant Mol. Biol., vol. 18, pp. 675–689, 1992.

Odell et al, Nature, vol. 313, pp. 810–812, 1985.

Rogers et al, J. Biol. Chem., vol. 258, pp. 8169–8174, 1983.

Schroeder et al, J. Biol. Chem., vol. 243, pp. 2943–2949, 1968.

Altenbach et al, Plant Mol. Biol., vol. 18, pp. 235–245, 1992.

Wim J. M. Van de Wen,et al., "Structure and Function of Eukaryotic Proprotein Processing Enzymes of the Subtilisin Family of Serine Proteases", *Critical Reviews in Oncogenesis* 4(2) 115–136 1993.

Takagi, Hiroshi, et al., "Enhancement of the Thermostability of Subtilisin E by Introduction of a Disulfide Bond Engineered on the Basis of Structural Comparison with a Thermophilic Serine Protease", *The Journal of Biological Chemistry* vol.265, No.12 pp. 6874–6878, Apr. 25, 1990.

Svendsen,I.B, "Chemical Modifications of The Subtilisins With Special Reference to the Binding of Large Substrates, A Review", Carlsberg Res. Commun. vol. 41, No. 5, 1976.

Pierce, Jeffrey A., et al., "Physiological and Genetic Strategies for Enhanced Subtilisin production by *Bacillus subtilis*", *Biotechnol. Prog.*, vol. 8, pp. 211–218, 1992.

Wells, James A., et al., "Subtilisin–an enzyme designed to be engineered", *Trends In Biochemical Sciences*, Aug. 1988.

Hiei, Yukoh, et al., "Efficient transformation of rice (*Oryza sativa* L.) mediated by Agrobacterium and sequence analysis of the boundaries of the T–DNA", *The Plant Journal* 6 (2), pp. 271–282 Jan. 1994.

Ishida, Yuji, et al., "High efficiency transformation of maize (*Zea mays* L.) mediated by Agrobacterium tumefaciens", *Nature biotechnology* vol. 14, pp. 745–750, Jun. 1996.

Cheng, Ming, et al., "Genetic Transformation of Wheat Mediated by Agrobacterium tumefaciens", *Plant Physiol* p. 971, 1997.

Bustos, Mauricio M., "Regulalion of B–Glucuronidase Expression in Transgenic Tobacco Plants by an A/T–Rich, cis–Acting Sequence Found Upstream of a French Bean B–Phaseolin Gene", *The Plant Cell*, vol. 1, Sep. 1989.

*Primary Examiner*—David T. Fox
*Assistant Examiner*—Ashwin D. Mehta
*Attorney, Agent, or Firm*—Patricia A. Sweeney

[57] ABSTRACT

Production of proteases in plants is set forth, whereby heterologous DNA encoding the protease is introduced into the plant and expression of the protein achieved. By such methods, expression is achieved in plants wherein the plant cell is not damaged, the protein can be recovered without contamination by other proteases, and can be expressed at levels such that commercial production of the enzyme is obtained. Expression levels can be at 0.1% of total soluble protein of the plant, or higher.

15 Claims, 4 Drawing Sheets

COMMERCIAL PRODUCTION OF PROTEASES IN PLANTS

BACKGROUND OF THE INVENTION

Commercial production of proteases that is high yielding, economical and provides ease in manufacture and processing would provide considerable advantages to many industries. Proteases are used in a variety of commercial applications, including pharmaceutical uses, medical processes, lab processes, in sequencing amino acids, among others. Many proteases used in such commercial applications are obtained from sources that are difficult and costly to maintain, that are not high yielding, and include undesirable contaminants.

Among the problems encountered are that either animal organs or bacteria are the common sources for proteases. For example, pepsin is obtained from gastric mucosa, carboxypeptidase A and B are obtained from the pancreas of animals, and leucine aminopeptidase from the kidney and intestinal mucosa. Contamination by undesirable components produced by the animal cells can impact the final product. Bacterial sources typically cannot produce the protease in reliable or sufficient quantity to be useful for commercial purposes. An example of proteases obtained from bacteria include subtilisin and themolysin, obtained from strains of Bacillus. As noted by James Wells and David Estell, "Most enzymes are expressed in minute amounts, and no generic solution is available for the expression of large amounts of an active enzyme from its cloned gene." Wells, J. and Estell, D. "Subtilisin: An Enzyme Designed to Be Engineered" *Trends in Biochemical Sciences* (a review) vol. 13 pp. 291–297.

By way of example, in the digestive process, a hormone action is triggered that releases digestive juice made by the pancreas. This juice contains several precursors or zymogens, including trypsinogen, and chymotrypsinogen, among others. Trypsinogen is a protein which is the precursor or zymogen molecule of trypsin. By action of enterokinase, which removes a hexapeptide from the $NH_2$-terminal end of the trypsinogen molecule, trypsin is formed. Trypsin is a protease which hydrolyzes the peptide bonds of the oligopeptides in the intestine by cleaving on the carboxyl side of lysine and arginine residues. Trypsin also activates chymotrypsinogen to chymotrypsin. Chymotrypsin hydrolyzes the peptide bonds involving phenylalanine, tyrosine and tryptophan.

Trypsin has a number of uses in the biological sciences and in the medical field An example is the use of trypsin in identifying the sequence of amino acids. It is useful in many processes where its' selective cleaving can be employed. For example, because its' cleavage is specific to select amino acids, it can be used to break down a polypeptide into fragments of known number. Importantly, this substrate specificity is also useful in converting biosynthetically produced molecules to preferred molecules. It is used in this manner to convert proinsulin to insulin by removal of the connecting peptide. Thus, trypsin has many commercially valuable uses.

The current source of trypsin is the organs of animals, with bovine and porcine pancreas the primary common source of the enzyme. There are numerous difficulties associated with obtaining trypsinogen or trypsin from these sources. One is that there is considerable contamination by other proteases. Chymotrypsin is one of the additional proteases in the contaminants that may cleave the product in an undesired manner.

Further, there are obvious expenses and handling concerns when shipping and using animal pancreas. They must be fresh, kept sterile, shipped in a manner to maintain freshness of the organ, and require special storage space of sufficient size to accommodate the animal organs. It also requires the care, feeding, and slaughtering of the animals that are the source. Additionally, some users of the end product have concerns about use of enzymes prepared from animal sources as components in human products.

Prior attempts to avoid these problems have included expressing trypsinogen in bacteria. A European patent application describes introducing trypsin and trypsinogen into *E coli*, and selecting for transformed bacteria by use of an antibiotic resistance marker. See Greaney, EP 0 587 68 1. They used a variety of *E. coli* host cells in the construction of vectors and expression systems. There, the inventors reported that while some bacterial strains expressed the protein, others would not.

The present invention overcomes these obstacles by providing for a plant having a heterologous DNA sequence that expresses a protease. In one preferred embodiment, the protease is trypsin or trypsinogen. The inventors have been able to achieve expression at commercially acceptable levels of production and provide for a homogeneous product which does not contain the contaminants associated with animal sources. Since the source is plant, other undesirable proteases produced in the host are not a problem. The inventors have also found there are advantages to expressing proteases in seed. The seed is rich in protease inhibitors, thus enhancing stability. This is an even further advantage when the protease is not the inactive zymogen, (such as trypsinogen) but the active protease (such as trypsin). The storage, shipping and expense associated with expressing the enzyme in plants is vastly superior to the animal or bacterial sources.

Thus, it is an object of the invention to provide for plants and plant cells having DNA comprising heterologous nucleotide sequences encoding a protease.

It is a further object of this invention to provide for expression of proteases at commercially acceptable levels.

Another object of the invention is to provide for production of proteases which is not contaminated with animal proteases and other contaminants.

Yet another object of the invention is to provide for production of proteases in seed.

A still further object of the invention is to provide for a method of production of proteases in a biomass of plants.

Another object of the invention is to provide for production of proteases which is economical and provides for ease in production and handling.

A further object of the invention is to provide for production of trypsin or trypsinogen in plants at commercially acceptable levels and without contamination from animal proteases.

These and the other objectives will become apparent by the description below.

All references cited herein are incorporated herein by reference.

SUMMARY OF THE INVENTION

The invention is production of proteases in plants at commercially acceptable levels by introducing into a plant, DNA encoding a heterologous nucleotide sequence encoding the protease. In a preferred embodiment of the invention, the DNA is linked to a promoter such that expression levels of 0.1% and higher may be achieved. Yet another embodiment provides for the protease to be trypsin or trypsinogen.

In another preferred embodiment of the invention, the protease is expressed in the seed of the plant. In one embodiment, the promoter may be ubiquitin. In another preferred embodiment, the protease encoding DNA is linked with a seed specific promoter, such as the phaseolin promoter. Another preferred aspect of the invention provides for use of a signal sequence in the DNA construct, and in yet another preferred embodiment, may be the barley alpha amylase signal sequence.

In accordance with a second aspect of the invention, a method of reproducing proteases in commercial quantities is provided by providing a biomass from a plurality of plants, of which at least certain plants contain a DNA molecule comprised of a heterologous nucleotide sequence encoding the protease, wherein the nucleotide sequence is operably linked to a promoter to effect expression of the protease by those plants. The plant or plant tissue can then be fed directly to the animal, or the protein extracted. Where the protein is used as a digestive enzyme it may be particularly advantageous to feed the plant to the animal.

DETAILED DESCRIPTION OF THE PREFERRED EMBODIMENTS

The present inventors have determined that commercial production of proteases in plants is not only feasible but also offers substantial advantages over the conventional approach of obtaining the protein from animal organs. Plant tissue as a raw material would be cheaper and more stable to store. Contamination by proteases that have an undesired impact on the product can be avoided, since they are not produced from an animal source. Use from a plant source also avoids concerns about products from animal sources applied in products for human use.

In accordance with the present invention, a DNA molecule comprising a transformation/expression vector is engineered to incorporate protease-encoding DNA. By protease-encoding DNA, it is also meant to include both the protease in its active form, and the inactive form which can then be activated. In an embodiment of the invention, the DNA molecule encodes trypsin (the protease) or trypsinogen (the inactive form). Trypsin and trypsinogen differ in that trypsin is missing the first six amino acids of trypsinogen. If trypsin were placed in the plant, like any protease, there is a high likelihood that it would digest plant proteins, resulting in cell death. This can be prohibited by expressing trypsin in the seed of the plant, which is rich in protease inhibitors. Trypsinogen is the pro-form of the enzyme, and not an active protease, thus allowing for expression of the zymogen without destroying its host. The proenzyme can later be readily converted to trypsin by cleaving the first six amino acids.

Genes encoding the proteins are well known. When referring to "trypsin" or "trypsinogen" it is meant to encompass fragments and variations of the protein that still retain the characteristics of the proteolytic enzyme, and all genes which encode the proteins that fall within the category or trypsin or trypsinogen. In one example, Greaney, supra, discloses chemically synthesized genes for both trypsin and trypsinogen. The gene used in the examples below was made publicly available through Genbank, as accession number P00760. Isolation and cloning of the trypsinogen molecule can be accomplished by one skilled in the art using standard methodology.

Therefore, a gene for use in the present invention can be subcloned in a vector of choice. In another example, it is possible to screen a cDNA library with anti-protease antibodies. The known methodologies used would include identification of the gene by hybridization with probes, PCR, probe/promoter/synthetic gene synthesis, sequencing, molecular cloning and other techniques which are well known to those skilled in molecular biology. While it is possible to synthesize the gene to reflect preferred codon usage in plants, and may be useful in increasing expression of select proteases, (See, Murray et al, Nucleic Acid Res. 17:477–498 (1980)), it may not be necessary in all cases, as was found with the gene used in the examples below.

A problem associated with expressing proteases, such as trypsin, in a plant is that since it is a protease it may digest the proteins in the plant resulting in cell death. As noted, this effect is avoided by directing expression of the protease to seed. The protease inhibitors in the seed inhibit this effect. In a preferred embodiment of the invention avoiding protein degradation in the plant is further aided by secretion of the protein to the cell wall of the plant. This may be accomplished by use of a signal sequence and in a preferred embodiment is the barley alpha amylase signal sequence. Rogers, *J. Biol. Chem.* 260:3731–3738 (1985), or brazil nut protein when used in canola. Use of the signal sequence can also assist in increasing expression levels.

Another alternative is to express the zymogen, such as trypsinogen, in the plant, which is the pro-form of the enzyme and not a protease. The plant's own proteases are sequestered in the vacuoles and thus will not break down the zymogen. Whether the protease or the zymogen is expressed, the signal sequence provides an additional benefit in increasing expression level of the protein. See Jones and Robinson, Tansley Review, 17:567–597 (1989). The construct is made such that a signal peptide is fused to the N-terminus of the mature protein sequence, allowing for normal cellular processing to cleave accurately the protein molecule and yield mature protein.

The methods available for putting together such a relatively short synthetic gene comprising the various modifications for improved expression described above can differ in detail. However, the methods generally include the designing and synthesis of overlapping, complementary synthetic oligonucleotides which are annealed and ligated together to yield a gene with convenient restriction sites for cloning. The methods involved are standard methods for a molecular biologist.

Once the gene has been isolated and engineered to contain some or all of the features described above, it is placed into an expression vector by standard methods. The selection of an appropriate expression vector will depend upon the method of introducing the expression vector into host cells. A typical expression vector contains prokaryotic DNA elements coding for a bacterial replication origin and an antibiotic resistance gene to provide for the growth and selection of the expression vector in the bacterial host; a cloning site for insertion of an exogenous DNA sequence, which in this context would code for the protease; eukaryotic DNA elements that control initiation of transcription of the exogenous gene, such as a promoter; and DNA elements that control the processing of transcripts, such as transcription termination/polyadenylation sequences. It also can contain such sequences as are needed for the eventual integration of the vector into the plant chromosome.

In a preferred embodiment, the expression vector also contains a gene encoding a selection marker which is functionally linked to a promoter that controls transcription initiation. For a general description of plant expression vectors and reporter genes, see Gruber et al, "Vectors for Plant Transformation" in *Methods of Plant Molecular Biology and Biotechnology* 89–119 (CRC Press, 1993).

Promoter elements employed to control expression of the protease and the selection gene, respectively, can be any plant-compatible promoter. Those can be plant gene promoters, such as, for example, the ubiquitin promoter, the promoter for the small subunit of ribulose-1, 5-bisphosphate carboxylase, or promoters from the tumor-inducing plasmids from *Agrobacterium tumefaciens*, such as the nopaline synthase and octopine synthase promoters, or viral promoters such as the cauliflower mosaic virus (CaMV) 19S and 35S promoters or the figwort mosaic virus 35S promoter. See Kay et al, *Science* 236:1299 (1987) and European patent application No. 0 342 926. See international application WO 91/19806 for a review of illustrative plant promoters suitably employed in the present invention. The range of available plant compatible promoters includes tissue specific and inducible promoters.

In one embodiment of the present invention, the exogenous DNA is under the transcriptional control of a plant ubiquitin promoter. Plant ubiquitin promoters are well known in the art, as evidenced by European patent application no. 0 342 926.

In a further preferred embodiment, a tissue specific promoter is provided to direct transcription of the DNA preferentially to the seed. One such promoter is the phaseolin promoter. See, Bustos et al. "Regulation of β-glucuronidase Expression in Transgenic Tobacco Plants by an A/T-Rich cis-Acting Sequence Found Upstream of a French Bean β-Phaseolin Gene" *The Plant Cell* Vol. 1, 839–853 (1989).

In another preferred embodiment, the selective gene is a glufosinate-resistance encoding DNA and in a preferred embodiment can be the phosphinothricin acetyl transferase ("PAT") or maize optimized PAT gene under the control of the CaMV 35S promoter. The gene confers resistance to bialaphos. See, Gordon-Kamm et al, *The Plant Cell* 2:603 (1990); Uchimiya et al, *Bio/Technology* 11:835 (1993), and Anzai et al, *Mol. Gen.* 219:492 (1989).

Obviously, many variations on the promoters, selectable markers and other components of the construct are available to one skilled in the art.

In accordance with the present invention, a transgenic plant is produced that contains a DNA molecule, comprised of elements as described above, integrated into its genome so that the plant expresses a heterologous protease-encoding DNA sequence. In order to create such a transgenic plant, the expression vectors containing the gene can be introduced into protoplasts, into intact tissues, such as immature embryos and meristems, into callus cultures, or into isolated cells. Preferably, expression vectors are introduced into intact tissues. General methods of culturing plant tissues are provided, for example, by Miki et al, "Procedures for Introducing Foreign DNA into Plants" in *Methods in Plant Molecular Biology and Biotechnology*, Glick et al (eds) pp. 67–68 (CRC Press 1993) and by Phillips et al, "Cell/Tissue Culture and In Vitro Manipulation" in *Corn and Corn Improvement* 3d Edit. Sprague et al (eds) pp. 345–387 (American Soc. Of Agronomy 1988). The selectable marker incorporated in the DNA molecule allows for selection of transformants.

Methods for introducing expression vectors into plant tissue available to one skilled in the art are varied and will depend on the plant selected. Procedures for transforming a wide variety of plant species are well known and described throughout the literature. See, for example, Miki et al, supra; Klein et al, *Bio/Technology* 10:268 (1992); and Weisinger et al., *Ann. Rev. Genet.* 22:421–477 (1988). For example, the DNA construct may be introduced into the genomic DNA of the plant cell using techniques such as microprojectile-mediated delivery, Klein et al., *Nature* 327:70–73 (1987); electroporation, Fromm et al., *Proc. Natl. Acad. Sci.* 82:5824 (1985); polyethylene glycol (PEG) precipitation, Paszkowski et al., *Embo J.* 3:2717–2722 (1984); direct gene transfer WO 85/01856 and EP No. 0 275 069; in vitro protoplast transformation U.S. Pat. No. 4,684,611; and microinjection of plant cell protoplasts or embryogenic callus. Crossway, *Mol. Gen. Genetics* 202:179–185 (1985). Co-cultivation of plant tissue with Agrobacterium tumefaciens is another option, where the DNA constructs are placed into a binary vector system. Ishida et al., "High Efficiency Transformation of Maize (*Zea mays* L.) mediated by *Agrobacterium tumefaciens*" *Nature Biotechnology* 14:745–750 (1996). The virulence functions of the *Agrobacterium tumefaciens* host will direct the insertion of the construct into the plant cell DNA when the cell is infected by the bacteria. See, for example Horsch et al., *Science* 233: 496–498 (1984), and Fraley et al., *Proc. Natl. Acad, Sci.* 80:4803 (1983).

Standard methods for transformation of canola are described by Moloney et al. "High Efficiency Transformation of Brassica napus using Agrobacterium Vectors" *Plant Cell Reports* 8:238–242 (1989). Corn transformation is described by Fromm et al, *Bio/Technology* 8:833 (1990) and Gordon-Kamm et al, supra. Agrobacterium is primarily used in dicots, but certain monocots such as maize can be transformed by Agrobacterium. U.S. Pat. No. 5,550,318. Rice transformation is described by Hiei et al., "Efficient Transformation of Rice (Oryza sativs L.) Mediated by Agrobacterium and Sequence Analysis of the Boundaries of the T-DNA" *The Plant Journal* 6(2):271–282 (1994, Christou et al, *Trends in Biotechnology* 10:239 (1992) and Lee et al, *Proc. Nat'l Acad. Sci. USA* 88:6389 (1991)). Wheat can be transformed by techniques similar to those used for transforming corn or rice. Sorghum transformation is described by Casas et al, supra and sorghum by Wan et al, *Plant Physiciol.* 104:37 (1994). Soybean transformation is described in a number of publications, including U.S. Pat. No. 5,015,580.

It is preferred to select the highest level of expression of the protease, and it is thus useful to ascertain expression levels in transformed plant cells, transgenic plants and tissue specific expression. One such method is an ELISA assay which uses biotinylated anti-trypsin or anti-trypsinogen polyclonal antibodies and a streptavidin-alkaline phosphatase conjugate. For example, an ELISA used for quantitative determination of trypsinogen or trypsin levels can be an antibody sandwich assay, which utilizes polyclonal rabbit antibodies obtained commercially. The antibody is conjugated to streptavidin-alkaline phosphatases for detection.

The levels of expression of the gene of interest can be enhanced by the stable maintenance of a protease encoding gene on a chromosome of the transgenic plant. Use of linked genes, with herbicide resistance in physical proximity to the trypsin or trypsinogen gene, would allow for maintaining selective pressure on the transgenic plant population and for those plants where the genes of interest are not lost.

With transgenic plants according to the present invention, the protease can be produced in commercial quantities. Thus, the selection and propagation techniques described above yield a plurality of transgenic plants which are harvested in a conventional manner. The plants can be fed to the animal, or the protein extracted from plant tissue of interest or total biomass, depending on how the enzyme is to be used. Protease extraction from biomass can be accomplished by known methods which are discussed, for example, by Heney and Orr, *Anal. Biochem.* 114:92–96 (1981).

It is evident to one skilled in the art that there can be loss of material in any extraction method used. Thus, a minimum level of expression is required for the process to be economically feasible. For the relatively small number of transgenic plants that show higher levels of expression, a genetic map can be generated, via conventional RFLP and PCR analysis, which identifies the approximate chromosomal location of the integrated DNA molecule. For exemplary methodologies in this regard, see Glick and Thompson, in *Methods in Plant Molecular Biology and Biotechnology* 269–84 (CRC Press 1993). Genetic mapping can be effected, first to identify DNA fragments which contain the integrated DNA and then to locate the integration site more precisely. This further analysis would consist primarily of DNA hybridizations, subcloning and sequencing. The information thus obtained would allow for the cloning of a corresponding DNA fragment from a plant not engineered with a heterologous protease gene. (Here, "corresponding" refers to a DNA fragment that hybridizes under stringent conditions to the fragment containing the protease encoding gene). The cloned fragment can be used for high level expression of another gene of interest. This is accomplished by introducing the other gene into the plant chromosome, at a position and in an orientation corresponding to that of the heterologous gene. The insertion site for the gene of interest would not necessarily have to be precisely the same as that of the trypsinogen or trypsin gene, but simply in near proximity. Integration of an expression vector constructed as described above, into the plant chromosome then would be accomplished via recombination between the cloned plant DNA fragment and the chromosome. Recombinants, where the gene of interest resides on the chromosome in a position corresponding to that of the highly expressed protease gene likewise should express the gene at high levels.

The following illustrates, but is not intended to limit the scope of the invention. It will be evident to one skilled in the art that variations and modifications are possible and fall within the scope and spirit of the invention.

Seed from the Westar variety of canola was transformed with constructs comprising elements according to the present invention, and have been deposited with the American Type Culture Collection (ATCC) in Rockville, Maryland, under Accession no. 209942. Trypsinogen has also been introduced into Hi-II maize plants. The constructs in question are designated p4347, p5443 and p8244. The first construct comprises the ubiquitin promoter, including the first exon and intron; the barley alpha amylase export signal sequence; a trypsinogen-encoding sequence; pinII terminator; 35S promoter and terminator with the moPAT (maize optimized PAT) selectable marker. The p5443 construct is the same, but with a repeating tandem trypsinogen encoding gene. The other construct comprises a phaseolin promoter, brazil nut protein signal sequence, with the trypsinogen encoding sequence and phaseolin terminator, all repeated in tandem, along with the selectable marker, 35S promoter and terminator and the PAT gene. The following provides further detail.

EXAMPLE 1

Isolation and Cloning of Trypsinogen Encoding DNA

The gene for cationic trypsinogen was cloned from bovine (Bos taurus) pancreas by the methods described here, with isolated RNA reverse transcribed into cDNA. The trypsinogen protein has 229 residues, with the first 6 residues (VDDDDK- V=valine; D=aspartate; K=Iysine) being cleaved to produce the active enzyme, trypsin. The Genbank accession number is P00760. The sequence is set forth below.

1 CTTCATCTTT CTGGCTCTCT TGGGAGCCGC TGTTGCTTTC CCCGTGGACG

51 ATGATGACAA GATCGTGGGC GGCTACACCT GTGGGGCAAA TACTGTCCCC

101 TACCAAGTGT CCCTGAACTC TGGCTACCAC TTCTGCGGGG GCTCCCTCAT

151 CAACAGCCAG TGGGTGGTGT CTGCGGCTCA CTGCTACAAG, TCCGGAATCC

201 AAGTGCGTCT GGGAGAAGAC AACATTAATG TCGTTGAGGG CAATGAGCAA

251 TTCATCAGCG CATCCAAGAG TATCGTCCAT CCCAGCTACA ACTCAAACAC

301 CTTAAACAAC GACATCATGC TGATTAAACT GAAATCAGCT GCCAGTCTCA

351 ACAGCCGAGT AGCCTCTATC TCTCTGCCAA CATCCTGTGC CTCTGCTGGC

401 ACCCAGTGTC TCATCTCTGG CTGGGGCAAC ACCAAAAGCA GTGGCACCAG

451 CTACCCTGAT GTCCTGAAGT GTCTGAAGGC TCCCATCCTA TCAGACAGCT

501 CTTGCAAAAG TGCCTACCCA GGCCAGATCA CCAGCAACAT GTTCTGTGCG

551 GGCTACCTGG AGGGCGGAAA GGACTCCTGC CAGGGTGACT CCGGTGGCCC

601 TGTGGTCTGC AGTGGAAAGC TCCAGGGCAT TGTCTCCTGG GGCTCTGGCT

651 GCGCTCAGAA AAACAAGCCT GGTGTCTACA CCAAGGTCTG CAACTACGTG

701 AGCTGGATTA AGCAGACCAT CGCCTCCAAC TAAATAGCTT CATCTCTTCA

751 TGACCCTCTC TGCTAGCCAG CTTCACCTTC CTCCCATCCT GAACGCACTA
801 CTTAAATAAA ATCATTTATA AAACC

EXAMPLE 2

Preparation of Plasmid p8244

Figure 1:
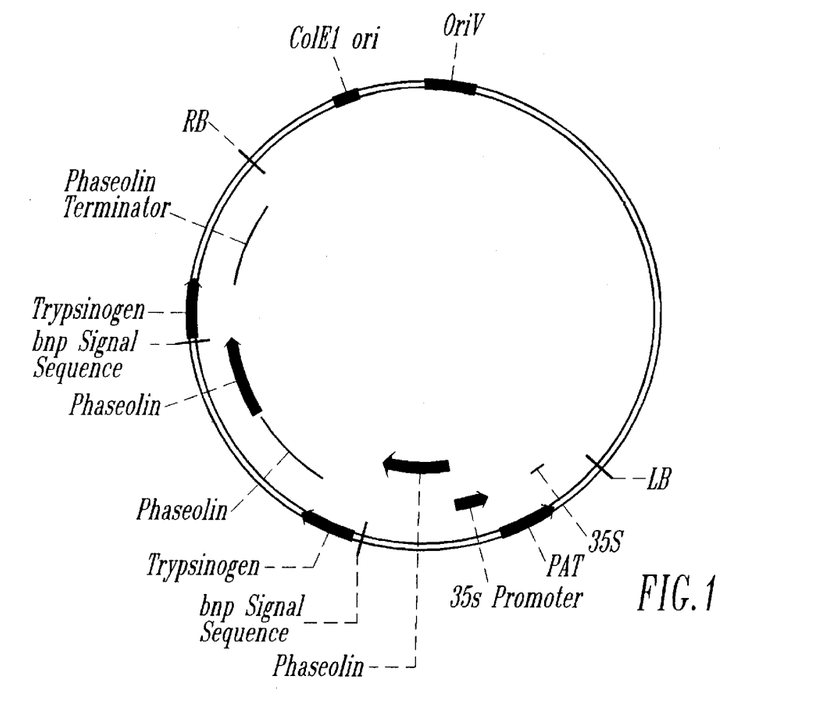
FIG. 1 shows p8244. In p8244, the trypsinogen gene is driven by the phaseolin promoter, and contains the brazil nut protein signal sequence, with the trypsinogen gene followed by the phaseolin terminator. A repeat of these sequences follows, with the selectable marker PAT gene driven by the CaMV35S promoter, and followed by the 35S terminator. The right and left borders of the T-DNA and replication origin sequences necessary for incorporation into the plant using Agrobacterium, are also included.

The canola trypsinogen expression plasmid was generated by first adding brazil nut protein signal sequence to the 5' end of the trypsinogen gene. An oligonucleotide was synthesized that contained the DNA codons for the brazil nut protein (bnp) transit peptide plus the codons for the first six amino acids of the trypsinogen protein. This oligonucleotide was annealed to the trypsinogen cDNA and the second strand filled in using PCR and the resulting fragment cloned into a pGEM vector. The bnp/trypsinogen fusion was removed from the pGEM vector using the restriction enzymes NcoI and HpaI and cloned into another plasmid, between a phaseolin promoter and terminator. The entire transcription unit with promoter and terminator was cut from this intermediate vector using Eco RI and NotI and the overhanging ends filled in with the Klenow fragment of DNA Polymerase I, generating blunt ended inserts. The insert was ligated into the filled EcoRI site of the binary vector pBIN19. Two inserts of the trypsinogen gene ligated end to end in this vector, generating p8244, (FIG. 1) which contains two complete transcription units for trypsinogen.

Preparation of Plasmid p4347

Figure 2:
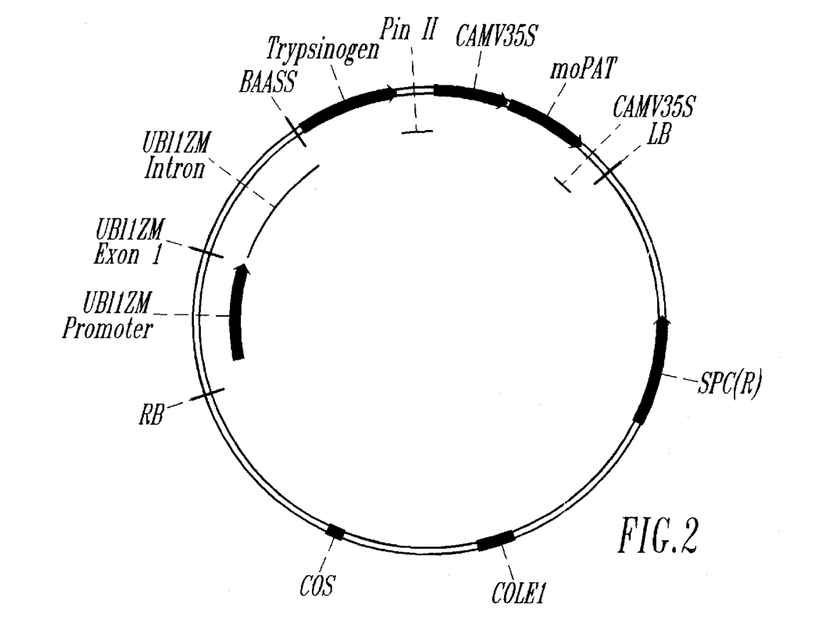
FIG. 2 shows p4347. In p4347, the trypsinogen gene is driven by the ubiquitin promoter which includes the first exon and intron, the barley alpha amylase signal sequence, and the trypsinogen gene followed by a PinII transcription termination sequence. The selectable marker, the moPAT gene is controlled by the CaMV35S promoter and terminator regions. The plasmid includes sequences necessary for incorporation into the plant using Agrobacterium, including the left and right borders of the T-DNA, the replication origin region, the co-integration site and spectinomycin resistance sequences as the selection agent.

PCR mutagenesis of p8244 was conducted to add a HpaI site to the 3' end of the coding region and the barley α-amylase signal sequence to the 5' end. The barley α-amylase sequence also contained a NcoI site at the start of the coding region. The NcoI/HpaI fragment was cloned into an intermediate cloning vector which had been cleaved with BpuAI and HpaI. The resulting construct contained the ubiquitin promoter, the trypsinogen open reading frame and the pinII terminator region. The construct was then cleaved with NheI and NotI and cloned into the vector p3770 which had been cleaved with NheI and NotI. This vector also contained the plant transcription unit comprised of the 35S promoter, the maize optimized PAT gene, and the 35S terminator region. The vector which resulted, p4347, (FIG. 2) contained two plant transcription units: the ubiquitin promoter, trypsinogen gene, PinII terminator; and the 35S promoter, the moPAT gene and the 35S terminator region.

Preparation of Plasmid p5443

Figure 3:
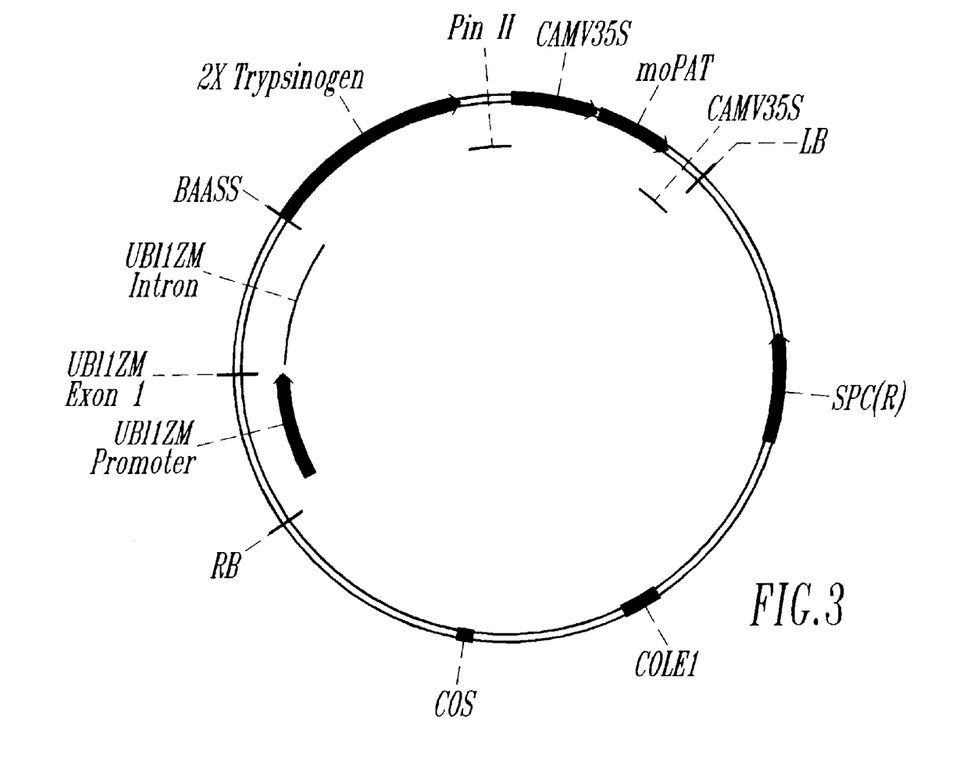
FIG. 3 shows p5443. It is essentially the same as p4347, except that tandem repeats of the trypsinogen gene are included.

PCR mutagenesis of p8244 was conducted to add a SalI site to the 5' end and 3' end of the coding region. The SalI site on the 5' end was designed to fuse the trypsinogen open reading frame in-frame with the trypsinogen gene. The SalI fragment was cloned into a cloning intermediate vector which had been cleaved with SalI. The resulting construct contained an open reading frame containing two copies of the trypsinogen gene. The NcoI/HpaI fragment from the construct was cloned into a cloning intermediate vector which had been cleaved with BpuAI and HpaI. The resulting construct contained the ubiquitin promoter, the trypsinogen open reading frame, and the PinII terminator region. The construct which resulted, p5443 (FIG. 3) contained two plant transcription units: the ubiquitin promoter, double trypsinogen gene, PinII terminator; and the 35S promoter, the moPAT gene and the 35S terminator region.

Preparation of Plasmid with Trypsin

Preparation of a plasmid will be carried out by the method described above, except that the trypsin gene instead of the trypsinogen gene will be used.

EXAMPLE 3

Transformation of Maize

Fresh immature zygotic embryos were harvested from Hi-II maize kernels at 1–2 mm in length. Fresh embryos were treated with 0.5 ml log phase Agrobacterium strains carrying the superbinary vectors designed by Japan Tobacco (Ishida, Y, H Saito, S Ohta, Y Hiei, T Komari and T Kumashiro. 1996. "High efficiency transformation of maize (*Zea mays L.*) mediated by *Agrobacterium tumefaciens*". *Nature Biotechnology* 14:745–750.). Bacteria were grown overnight in a rich medium with appropriate antibiotics to an optical density of 0.5, pelleted, then resuspended to the same density in a microfuge tube in a standard liquid Murishige and Skoog medium containing 100 µM acetosyringone. Embryos (5–10 per tube) were sonicated in the presence of the bacteria for 30 sec (Trick H and J Finer. 1997. "SAAT: sonication-assisted Agrobacterium-mediated transformation." *Transgenic Research* 6-.329–336), then plated on a solid medium as above. Embryos and bacteria were co-cultivated for 5 days.

Embryos not subjected to sonication will be transferred to a bialaphos selective agent on embryonic callus medium and transferred thereafter every two weeks to allow growth of transformed type II callus. Plants are regenerated from the callus.

Transformation of Canola

Plasmid p8244 was introduced into *Agrobacterium tumefaciens* strain EHA105 by electroporation. This strain was co-cultivated with canola cotyledons as per the published method of Moloney et al. supra. This method includes cutting petioles of 4.5 day germinated seedlings above the node, then dipping the base of the petiole in a suspension of Agrobacterium diluted to 0.05 OD 600, co-cultivating without selection for 2–3 days at 25° C. and 100 $\mu Em^2 s^1$ light intensity, then placing the cotyledons on selection medium containing 4 mg/L ppt (phosphinothricin-glufosinate ammonium). After 4–6 weeks on selection, shoots are removed and placed on rooting medium containing isobutyric acid. Rooted shoots are planted in soil and grown in the greenhouse for seed production.

EXAMPLE 4

Expression of trypsinogen in canola and corn was confirmed, and expression level of this protein is 0.1%–1% of soluble protein from canola seed. The protein in canola has been assayed by Western blots, by ELISA, and by activity assay as described below. Results are summarized in Table 1.

TABLE 1

Canola Transformation and Expression of Trypsinogen

| Event | Method | Expression Level I |
|---|---|---|
| 1, T1 seed | western | 0.1% |
| 1, T1 seed | enzyme assay | 0.15% |
| 1, T1 seed | quant. western | 1.0% |
| 1, T2 seed | ELISA | 0.18% |
| 1, T3 seed | ELISA | 0.4% |
| 1, T3 seed | western | 0.1% |

The corn tissue was analyzed by ELISA and transient expression of trypsin at 19% total soluble protein confirmed. Stable expression will be analyzed and is expected to confirm stable expression. Expression levels of 0.1% and higher are expected.

The Enzyme Linked Immunosorbent Assay was performed on canola using anti-trypsinogen polyclonal antibodies and streptavidin alkaline phosphatase. The seed extracts were combined with buffering solution. After centrifiction and decanting, total protein concentration is assayed and adjusted to one concentration with PBST (phosphate buffer saline with 0.05% v/v polyoxyethylene-sorbitan monolaureate (Tween-20)). Anti-trypsin antibodies were dispensed and incubated. After washing the plate with PBST, 10% normal rabbit serum and PBST were added and incubated. Trypsinogen standards were prepared and adjusted to the same protein concentration as the test samples. This was added to the well along with the test extracts. The plates were washed and diluted with biotinylated anti-trypsinogen antibodies diluted with PBST and 10% normal rabbit serum and added. Following incubation, the plate was washed and streptavidin-alkaline phosphatase conjugate diluted with PBST and 10% normal rabbit serum added and incubated. The plate was washed and pNPP substrate solution added and incubated. The plate was read and amount of target protein calculated by interpolation from the standard curve.

Activity of the enzyme was measured using a procedure in which antisera from four rabbits immunized with trypsinogen were pooled and the IgG fraction was purified using a Protein A agarose column. Protein concentration was determined using the $A_{280}$ spectrophotometric method. Fifty milligrams of pure IgG was buffer exchanged into coupling buffer (50 mM sodium acetate, pH 5.0) using 3 PD-10 columns, eluting in 10.5 ml coupling buffer. 1.05 ml of 0.1M sodium periodate in water was added to the IgG and the solution incubated for 1 hour at room temperature. The unreacted periodate was removed by passing the solution over 4 PD-10 columns equilibrated with coupling buffer. The oxidized antibody was then incubated overnight at 4° C. with 10 ml of hydrazide AX resin that had been pre-equilibrated with coupling buffer. After coupling, the supernatant is removed and checked for residual IgG. The resin was then washed sequentially with coupling buffer, washing buffer (PBS+0.5M NaCl) and PBST by resuspending in approximately 5 volumes of buffer followed by centrifugation to collect resin with a minimum of three repetitions for each buffer. The resin was then stored as a 1:1 suspension in PBST+0.1% thimersol. Samples containing trypsinogen were incubated with 25 μl of resin overnight to capture the enzyme.

These samples were activated with 1.0 U/sample enterokinase in 200 μl activation buffer for one hour at room temperature with constant mixing. The activation mixture was removed and the samples washed with =1.0 ml of activation buffer and =1.0 ml of development buffer (0. 1M TRIS, pH 8.0) while under constant vacuum. Immediately after the removal of the development buffer wash, the samples were developed with 0.125 mM Chromozyma® TRY (Boehringer Mannheim Biochemicals) enzyme substrate in development buffer at room temperature for 1 hour on a microtiter plate shaker. The resulting yellow supernatant is removed by gentle vacuum to a separate Dynatech microtiter plate and the samples were analyzed on a SpectroMax microtiter plate reader (Molecular Devices, Sunnyvale Calif.) at 405 nm. The concentration of trypsinogen in the sample is determined by comparison to a standard curve.

Southern analysis is a well known technique to those skilled in the art. This common procedure involves isolating the plant DNA, cutting with restriction endonucleases and fractionating the cut DNA on an agarose gel to separate the DNA by molecular weight and transferring to nitrocellulose membranes. It is then hybridized with the probe fragment which was radioactively labeled with $^{32}$P and washed in an SDS solution. Southern, E., or "Detection of a specific sequences among DNA fragments by gel electrophoresis "*J. Mol. Biol*. 98:503–517 (1975). Northern analysis is also a commonly used technique by those skilled in the art and is similar to Southern analysis except that RNA is isolated and placed on an agarose gel. The RNA is then hybridized with a labeled probe. Potter, E. et al. "Thyrotropin releasing hormone exerts rapid nuclear effects to increase production of the primary prolactin mRNA transcript" *Proc. Nat. Acad. Sci. U.S.A.* 78:6662–6666 (1981). A Western analysis is a variation of this technique, where instead of isolating DNA, the protein of interest is isolated and placed on an acrylamide gel. The protein is then blotted onto a membrane and contacted with a labeling substance. (See e.g,Hood et al. "Commercial Production of Avidin from Transgenic Maize; Characterization of Transformants, Production, Processing, Extraction and Purification" *Molecular Breeding* 3:291–306 (1997))

Here, Western analyses were performed as described, with samples electrophoresed and the gel blotted followed by incubation overnight with anti-trypsinogen IgG diluted in blocking buffer. The blot was then washed three times with PBST and incubated with 1:5000 dilution of anti-rabbit peroxidase conjugate in blocking buffer and developed.

Figure 4A:
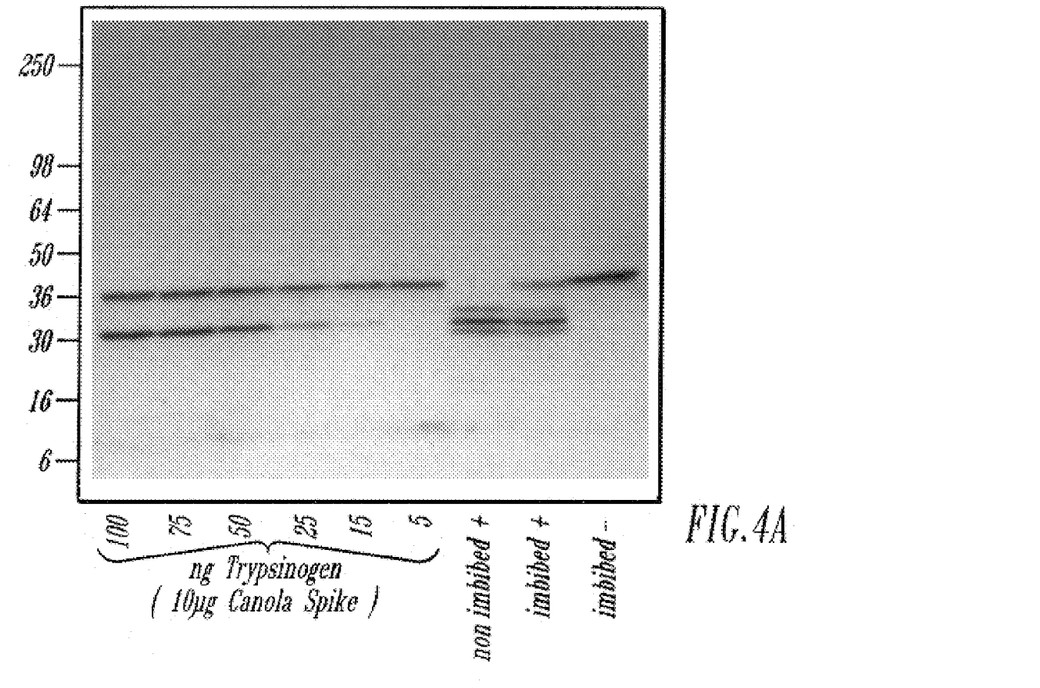
FIGS. 4A and 4B are Western gel blots of protein extracted from transformed canola seed expressing trypsinogen, and controls.
Figure 4B:
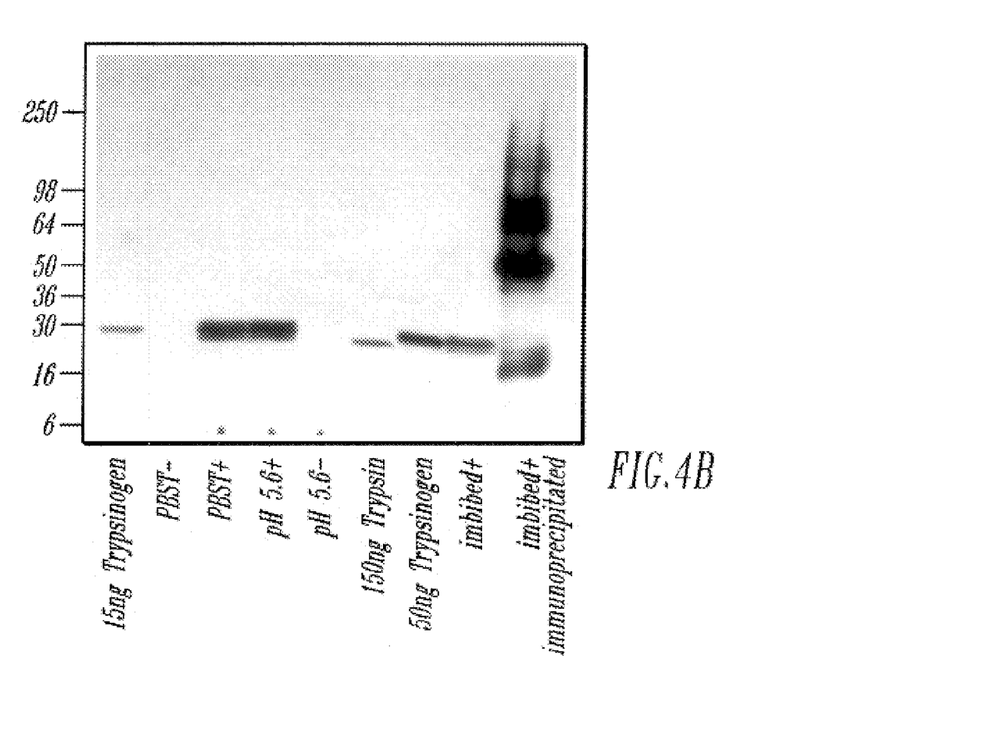

Western blots of trypsinogen positive canola seed are shown in FIGS. 4A and B. In 4A the first six lanes show differing amounts of commercial trypsinogen, used to provide a standard curve. The next three lanes represent extracts from transformed canola seeds: the first was extract from dry seed of a trypsinogen positive plant; the second was extract from seed of a trypsinogen positive plant that was imbibed in water overnight; the third was extract from seed of a trypsinogen negative plant, imbibed in water overnight.

FIG. 4B is another Western blot, with the first lane showing a control of 15 ng of commercially produced trypsinogen, the second of control seed extracted with PBST. The third lane is trypsinogen positive seed extracted with PBST, and the fourth is the seed extracted with a pH 5.6 buffer. The fifth lane is control seed extracted with a pH5.6 buffer. The sixth lane is 150 ng of commercial mature trypsinogen, (i.e., trypsin) followed by 50 ng of control trypsinogen. The eighth and ninth lanes are extract of transformed trypsinogen positive seed with the eighth imbibed in water and the last lane immunoprecipitated. In the three bands of the canola seed extract, the terminal sequence of the center band matches mature trypsinogen.

Figure 5A:
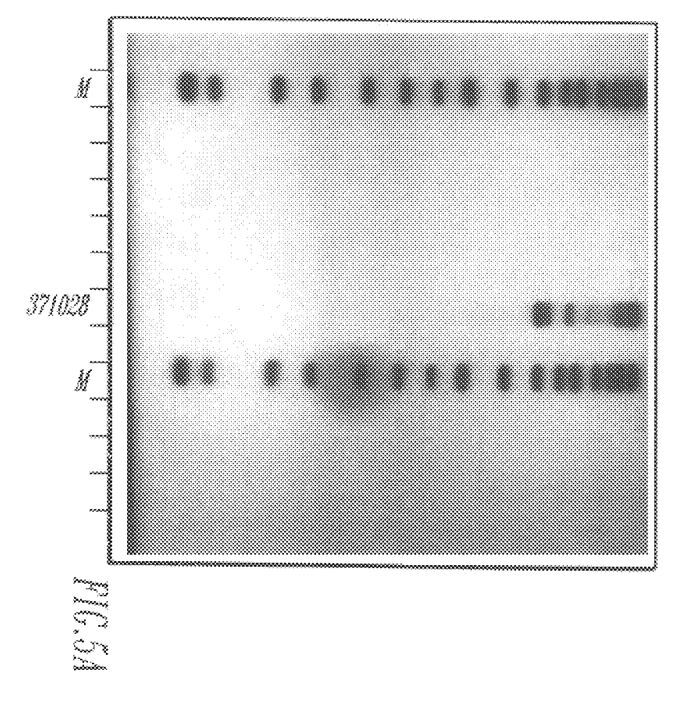
FIGS. 5A and 5B are Southern gel blots of DNA extracted from transformed canola plants expressing trypsinogen in the seed.
Figure 5B:
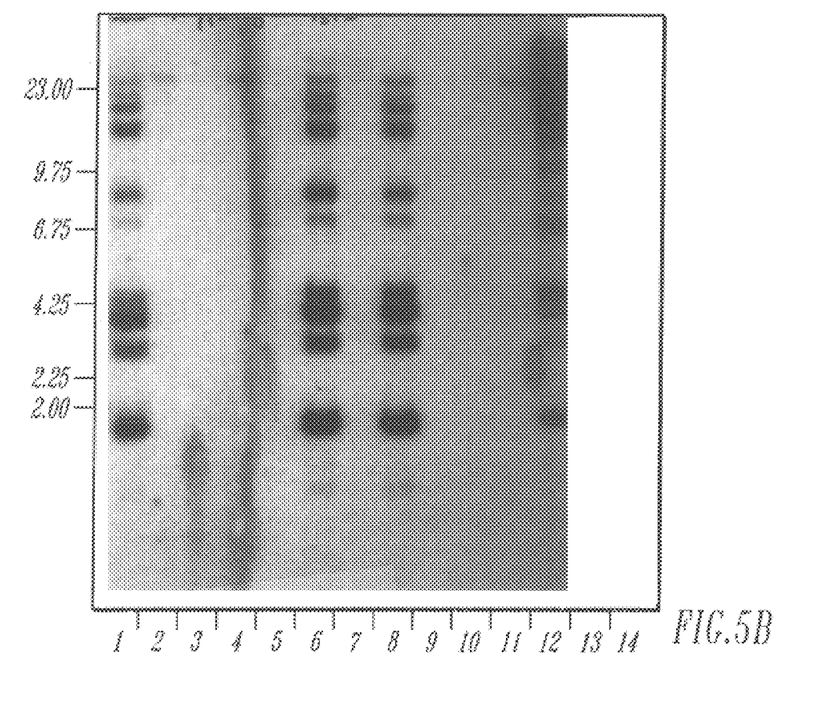

A Southern analysis was performed as described, with DNA extracted from a $T_0$ plant, digested with HindIII, and hybridized with the PAT gene as a probe. The results are shown in FIG. 5A. The results show that one PCR positive plant that showed resistance to glufosinate exposure hybridized to the PAT gene. Five bands showed clear hybridization. FIG. 5B shows another southern blot, of the $T_3$ progeny of the transformation event used in the analysis shown in 5A. Fourteen of the progeny were screened. DNA was extracted, digested with PstI and hybridized with the trypsinogen gene as a probe. After screening for glufosinate resistance and by PCR, the Southern analysis showed four plants were positive for trypsinogen. The restriction enzyme digests indicated three insertions of the T-DNA occurred.

A Northern blot analysis will be performed on canola and is expected to reflect expression of trypsinogen.

EXAMPLE 5

The plasmid containing the trypsin gene will be introduced into corn cells via the method described above, and expression determined using ELISA, western blot and activity assay. The analysis is expected to confirm expression of trypsin in the plant. Levels of expression are expected to be at 0.1% or higher.

Thus it is believed the invention accomplishes at least all of its objectives.

What is claimed is:

1. A transgenic plant comprising a DNA molecule comprised of a heterologous nucleotide sequence coding for an inactive proenzyme form of a protease, wherein the nucleotide sequence is linked to a promoter to effect expression of the protease in the plant such that when the protease is expressed the degradation of proteins in the plant due to said protease is reduced such that the plant can continue to function and the protease can be expressed during plant development.

2. The transgenic plant of claim 1 wherein the protease is trypsinogen.

3. The transgenic plant of claim 1 comprising plant tissue wherein the protease is expressed at levels of about 0.1% or higher of soluble protein expressed in the plant tissue.

4. The transgenic plant of claim 3 wherein the protease is trypsinogen.

5. The transgenic plant of claim 1 wherein the plant produces seed, the DNA molecule expresses the protease preferentially in seed of the plant.

6. The transgenic plant of claim 1 comprising plant cells wherein the DNA molecule expresses the protease preferentially in the cell wall of the plant cell.

7. The transgenic plant of claim 1 wherein the plant is a corn plant.

8. The transgenic plant of claim 1 wherein the plant is a canola plant.

9. The transgenic plant of claim 1 wherein the plant is canola, germplasm of which is deposited under ATCC accession no. 209942.

10. Plant cells of the plant of claim 1.

11. Plant cells of claim 10 wherein the protease is trypsinogen.

12. A method of producing protease in commercial quantities, comprising providing biomass from a plurality of plants, of which a commercially-adequate protease producing number of plants contain a DNA molecule comprised of a heterologous nucleotide sequence coding for the inactive proenzyme form of the protease, wherein the nucleotide sequence is operably linked to a promoter to effect expression of the protease by the protease producing plants, such that when the protease is expressed the degradation of proteins in the plant due to said protease is reduced such that the plant can continue to function and the protease can be expressed during plant development and extracting the protease from the biomass.

13. The method of claim 12 wherein the protease is trypsinogen.

14. The method of claim 12, wherein the DNA molecule is preferentially expressed to seed of the plants, and the biomass is comprised of seeds.

15. The method of claim 14 wherein the protease is trypsinogen.

* * * * *

SEQUENCE LISTING

<160> NUMBER OF SEQ ID NOS: 2

<210> SEQ ID NO 1
<211> LENGTH: 825
<212> TYPE: DNA
<213> ORGANISM: Bos taurus
<220> FEATURE:
<221> NAME/KEY: CDS
<222> LOCATION: (44)..(730)

<400> SEQUENCE: 1

```
cttcatcttt ctggctctct tgggagccgc tgttgctttc ccc gtg gac gat gat      55
                                                  Val Asp Asp Asp
                                                   1 gac aag atc gtg ggc ggc tac acc tgt ggg gca aat act gtc ccc tac     103
Asp Lys Ile Val Gly Gly Tyr Thr Cys Gly Ala Asn Thr Val Pro Tyr
 5                  10                  15                  20 caa gtg tcc ctg aac tct ggc tac cac ttc tgc ggg ggc tcc ctc atc     151
Gln Val Ser Leu Asn Ser Gly Tyr His Phe Cys Gly Gly Ser Leu Ile
                25                  30                  35 aac agc cag tgg gtg gtg tct gcg gct cac tgc tac aag tcc gga atc     199
Asn Ser Gln Trp Val Val Ser Ala Ala His Cys Tyr Lys Ser Gly Ile
            40                  45                  50 caa gtg cgt ctg gga gaa gac aac att aat gtc gtt gag ggc aat gag     247
Gln Val Arg Leu Gly Glu Asp Asn Ile Asn Val Val Glu Gly Asn Glu
        55                  60                  65 caa ttc atc agc gca tcc aag agt atc gtc cat ccc agc tac aac tca     295
Gln Phe Ile Ser Ala Ser Lys Ser Ile Val His Pro Ser Tyr Asn Ser
 70                  75                  80 aac acc tta aac aac gac atc atg ctg att aaa ctg aaa tca gct gcc     343
Asn Thr Leu Asn Asn Asp Ile Met Leu Ile Lys Leu Lys Ser Ala Ala
 85                  90                  95                 100 agt ctc aac agc cga gta gcc tct atc tct ctg cca aca tcc tgt gcc     391
Ser Leu Asn Ser Arg Val Ala Ser Ile Ser Leu Pro Thr Ser Cys Ala
                105                 110                 115 tct gct ggc acc cag tgt ctc atc tct ggc tgg ggc aac acc aaa agc     439
Ser Ala Gly Thr Gln Cys Leu Ile Ser Gly Trp Gly Asn Thr Lys Ser
            120                 125                 130 agt ggc acc agc tac cct gat gtc ctg aag tgt ctg aag gct ccc atc     487
Ser Gly Thr Ser Tyr Pro Asp Val Leu Lys Cys Leu Lys Ala Pro Ile
        135                 140                 145 cta tca gac agc tct tgc aaa agt gcc tac cca ggc cag atc acc agc     535
Leu Ser Asp Ser Ser Cys Lys Ser Ala Tyr Pro Gly Gln Ile Thr Ser
    150                 155                 160 aac atg ttc tgt gcg ggc tac ctg gag ggc gga aag gac tcc tgc cag     583
Asn Met Phe Cys Ala Gly Tyr Leu Glu Gly Gly Lys Asp Ser Cys Gln
165                 170                 175                 180 ggt gac tcc ggt ggc cct gtg gtc tgc agt gga aag ctc cag ggc att     631
Gly Asp Ser Gly Gly Pro Val Val Cys Ser Gly Lys Leu Gln Gly Ile
                185                 190                 195 gtc tcc tgg ggc tct ggc tgc gct cag aaa aac aag cct ggt gtc tac     679
Val Ser Trp Gly Ser Gly Cys Ala Gln Lys Asn Lys Pro Gly Val Tyr
                200                 205                 210
```

-continued

```
acc aag gtc tgc aac tac gtg agc tgg att aag cag acc atc gcc tcc         727
Thr Lys Val Cys Asn Tyr Val Ser Trp Ile Lys Gln Thr Ile Ala Ser
        215                 220                 225 aac taaatagctt catctcttca tgaccctctc tgctagccag cttcaccttc               780
Asn ctcccatcct gaacgcacta cttaaataaa atcatttata aaacc                        825
```

<210> SEQ ID NO 2
<211> LENGTH: 229
<212> TYPE: PRT
<213> ORGANISM: Bos taurus

<400> SEQUENCE: 2

```
Val Asp Asp Asp Lys Ile Val Gly Gly Tyr Thr Cys Gly Ala Asn
 1               5                  10                  15

Thr Val Pro Tyr Gln Val Ser Leu Asn Ser Gly Tyr His Phe Cys Gly
            20                  25                  30

Gly Ser Leu Ile Asn Ser Gln Trp Val Val Ser Ala Ala His Cys Tyr
        35                  40                  45

Lys Ser Gly Ile Gln Val Arg Leu Gly Glu Asp Asn Ile Asn Val Val
    50                  55                  60

Glu Gly Asn Glu Gln Phe Ile Ser Ala Ser Lys Ser Ile Val His Pro
65                  70                  75                  80

Ser Tyr Asn Ser Asn Thr Leu Asn Asn Asp Ile Met Leu Ile Lys Leu
                85                  90                  95

Lys Ser Ala Ala Ser Leu Asn Ser Arg Val Ala Ser Ile Ser Leu Pro
            100                 105                 110

Thr Ser Cys Ala Ser Ala Gly Thr Gln Cys Leu Ile Ser Gly Trp Gly
        115                 120                 125

Asn Thr Lys Ser Ser Gly Thr Ser Tyr Pro Asp Val Leu Lys Cys Leu
    130                 135                 140

Lys Ala Pro Ile Leu Ser Asp Ser Ser Cys Lys Ser Ala Tyr Pro Gly
145                 150                 155                 160

Gln Ile Thr Ser Asn Met Phe Cys Ala Gly Tyr Leu Glu Gly Gly Lys
                165                 170                 175

Asp Ser Cys Gln Gly Asp Ser Gly Gly Pro Val Val Cys Ser Gly Lys
            180                 185                 190

Leu Gln Gly Ile Val Ser Trp Gly Ser Gly Cys Ala Gln Lys Asn Lys
        195                 200                 205

Pro Gly Val Tyr Thr Lys Val Cys Asn Tyr Val Ser Trp Ile Lys Gln
    210                 215                 220

Thr Ile Ala Ser Asn
225
```